(12) United States Patent
Unfors

(10) Patent No.: US 9,405,021 B2
(45) Date of Patent: Aug. 2, 2016

(54) DETECTOR FOR DETECTING X-RAY RADIATION PARAMETERS

(71) Applicant: Unfors RaySafe AB, Billdal (SE)

(72) Inventor: Tomas Unfors, Billdal (SE)

(73) Assignee: Unfors Raysafe AB, Billdal (SE)

( * ) Notice: Subject to any disclaimer, the term of this patent is extended or adjusted under 35 U.S.C. 154(b) by 143 days.

(21) Appl. No.: 13/908,327

(22) Filed: Jun. 3, 2013

(65) Prior Publication Data

US 2014/0353514 A1  Dec. 4, 2014

(51) Int. Cl.
*G01T 1/02* (2006.01)
*G01T 1/29* (2006.01)

(52) U.S. Cl.
CPC .................... *G01T 1/2928* (2013.01)

(58) Field of Classification Search
CPC .................................... A61N 5/1048
USPC .................................... 250/370.09
See application file for complete search history.

(56) References Cited

U.S. PATENT DOCUMENTS

| | | |
|---|---|---|
| 4,365,341 A | 12/1982 | Lam |
| 4,675,892 A | 6/1987 | Plessis et al. |
| 4,891,522 A | 1/1990 | Coon et al. |
| 4,918,714 A | 4/1990 | Adamski et al. |
| 5,821,540 A | 10/1998 | Sato et al. |
| 8,184,766 B2 | 5/2012 | Fuchs et al. |
| 2005/0100133 A1 | 5/2005 | Reinhold |
| 2007/0195929 A1* | 8/2007 | Ruchala et al. ................. 378/65 |
| 2011/0049377 A1* | 3/2011 | Morf et al. ............... 250/370.14 |
| 2011/0112351 A1* | 5/2011 | Fordyce et al. .................... 600/1 |
| 2011/0215250 A1* | 9/2011 | Ohta et al. ................ G01T 1/24 250/370.08 |
| 2013/0223594 A1* | 8/2013 | Sprong et al. ................... 378/62 |

FOREIGN PATENT DOCUMENTS

| | | |
|---|---|---|
| DE | 19611228 | 10/1997 |
| DE | 19618122 | 11/1997 |
| GB | 2069129 | 8/1981 |

OTHER PUBLICATIONS

International Search Report and Written Opinion from corresponding International Application No. PCT/SE2014/050662, mailed on Oct. 10, 2014.

* cited by examiner

*Primary Examiner* — David J Makiya
*Assistant Examiner* — Kenneth J Malkowski
(74) *Attorney, Agent, or Firm* — Renner, Otto, Boisselle and Sklar, LLP

(57) ABSTRACT

The present invention relates to an X-ray parameter measuring arrangement comprising a detector for measuring said parameter configured to be positioned in a position adjacent to an x-ray source arranged to generate a ray formation having a primary ray portion for radiating an object. The position is chosen in such a way that the interference with a reproduced image is reduced or eliminated.

15 Claims, 5 Drawing Sheets

DETECTOR FOR DETECTING X-RAY RADIATION PARAMETERS

TECHNICAL FIELD

The present invention relates generally to providing dose measurement in an X-ray apparatus, and in particular to an X-ray dose detection arrangement, an X-ray imaging system, and a method for measuring an X-ray dose in an X-ray imaging system.

BACKGROUND

In X-ray imaging, for example in medical X-ray imaging, it is necessary to control radiation levels. Therefore, the X-ray dose is measured, for example by providing an ionization chamber. The ionization chamber may be provided as an extra-unit between the object, for example a patient, and the detector/x-ray source. However, due to the ionization chamber provided as a separate component, the setup for the X-ray imaging system consumes valuable space. Further, the ionization chamber may be displaced and exposure procedures may be performed without ionization chambers.

FIG. 1 is a schematic view of a simplified X-ray source housing 100 according to prior art. The X-ray source housing 100 comprises an X-ray tube 101, which generates X-rays 102. The X-rays 102 pass through a collimator 103 and in this case a Dose Area Product (DAP) meter 104.

DAP meters are usually large-area, transmission ionization chambers and associated electronics. In use, the ionization chamber is placed perpendicular to the beam central axis and in a location to completely intercept the entire area of the x-ray beam. The DAP, in combination with information on x-ray field size can be used to determine the average dose produced by the x-ray beam at any distance downstream in the x-ray beam from the location of the ionization chamber.

DAP is defined as the integral of dose across the X-ray beam. Therefore DAP includes field non-uniformity effects such as anode-heel-effect, and the use of semi-transparent beam-equalizing shutters (lung shutter). Assuming that the incident beam is totally confined to the patient, the recorded value may essentially provide an upper limit on the X-ray energy absorbed by the patient (i.e. there is no transmission or scatter). DAP's ability to estimate stochastic risk is degraded because of the lack of dose distribution information within the patient. The best may be to assume an average weighting factor for all the tissues at risk. This may lead to an over or under estimate of risk in certain cases.

SUMMARY

Thus, there is a need to provide dose measurement in X-ray imaging requiring minimized constructional space and positioning that do not interfere with the reproduced image. The solution of the present invention provides for measuring a number of X-ray parameters, amongst others total dose and ray quality.

For these reasons an X-ray parameter measuring arrangement comprising a detector for measuring said parameter configured to be positioned in a position adjacent to an x-ray source arranged to generate a ray formation having a primary ray portion for radiating an object. The position is chosen in such a way that the interference with a reproduced image is reduced or eliminated. In one embodiment, the detector is configured to measure scattered radiation. In another embodiment, the detector is configured to measure a direct radiation. In one embodiment, the detector is arranged on a housing of the x-ray source and configured to detect the scattered rays through an aperture provided in the housing. The detector, according to a second embodiment, is arranged at an opening of a housing of the source from which x-rays emerge, positioned at least partly or entirely in an image field, i.e. the ray formation radiating an object to be examined. The detector may also be arranged inside a housing of the source, in a position of corresponding to a direction from where the rays leave a collimator aperture positioned at least partly or entirely in an image field, i.e. the ray formation radiating an object to be examined. In a fourth, the detector is arranged inside a housing, between the source and a collimator. In a fifth embodiment, the detector is arranged inside or on a surface of a collimator.

The X-ray parameter measuring arrangement of the present invention, may be configured to measure one or several radiological parameters including dose of scattered X-rays, total dose, dose rate, Peak Kilovoltage (kVp), half-value layer (HVL), total filtration, exposure time, pulses, pulse rate and dose/pulse.

The detector, in one embodiment, comprises a housing enclosing a number of stacked diode layers, each diode layer distanced from each other and provided with a radiation filter between each diode layer and each diode layer connected to a processing unit for generating a signal corresponding to said parameter. The detector may comprise a housing enclosing one or several diodes in one layer. Moreover, the detector in one embodiment comprises a RF communication portion.

The invention also relates to an X-ray detector comprising: a number of stacked diode layers, a radiation filter layer between each diode layer; and a processing unit connected each diode layer or a diode in each diode layer. The X-ray detector may further comprise a housing of a radiation blocking material. The processing unit may be realized in Application Specific Integrated Circuit (ASIC).

The invention also relates to a computer network for handling radiological information, the network comprising an X-ray examination arrangement, a data collector and a database, wherein the X-ray examination arrangement is provided with an X-ray parameter measuring arrangement comprising a detector for measuring said x-ray parameter, the arrangement is configured to be positioned in a position adjacent to an x-ray source arranged to generate a ray formation having a primary ray portion for radiating an object.

The position is chosen in such a way that the interference with a reproduced image is reduced or eliminated. The database may consist of a central application and a locally-installed DICOM or MWL, RDSR, MPPS, DICOMOCR data collector.

BRIEF DESCRIPTION OF THE DRAWINGS

Reference is made to the attached drawings, wherein elements having the same reference number designation may represent like elements throughout.

FIG. 2b illustrates schematically an exaggerated portion of X-ray source of FIG. 2a;

DETAILED DESCRIPTION

Figure 1:
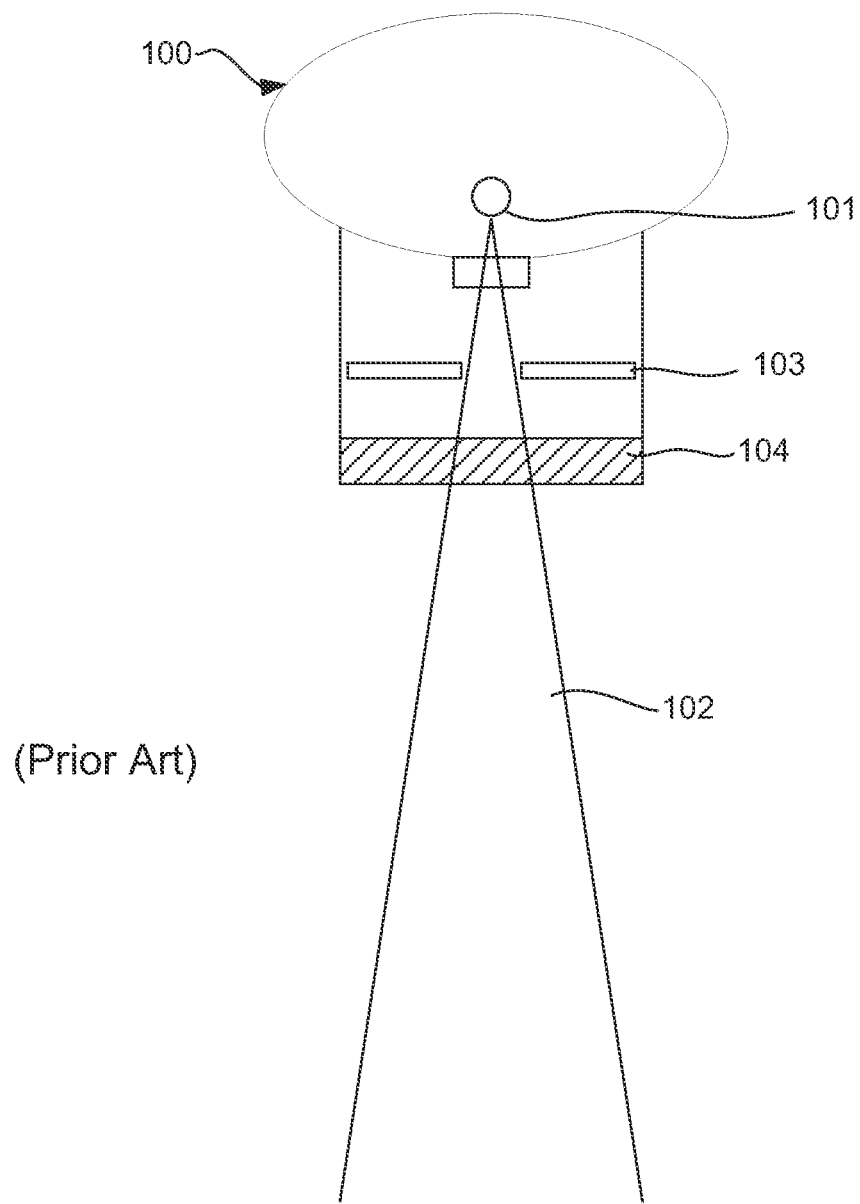
FIG. 1 illustrates schematically an exemplary X-ray source according to prior art.
Figure 2A:
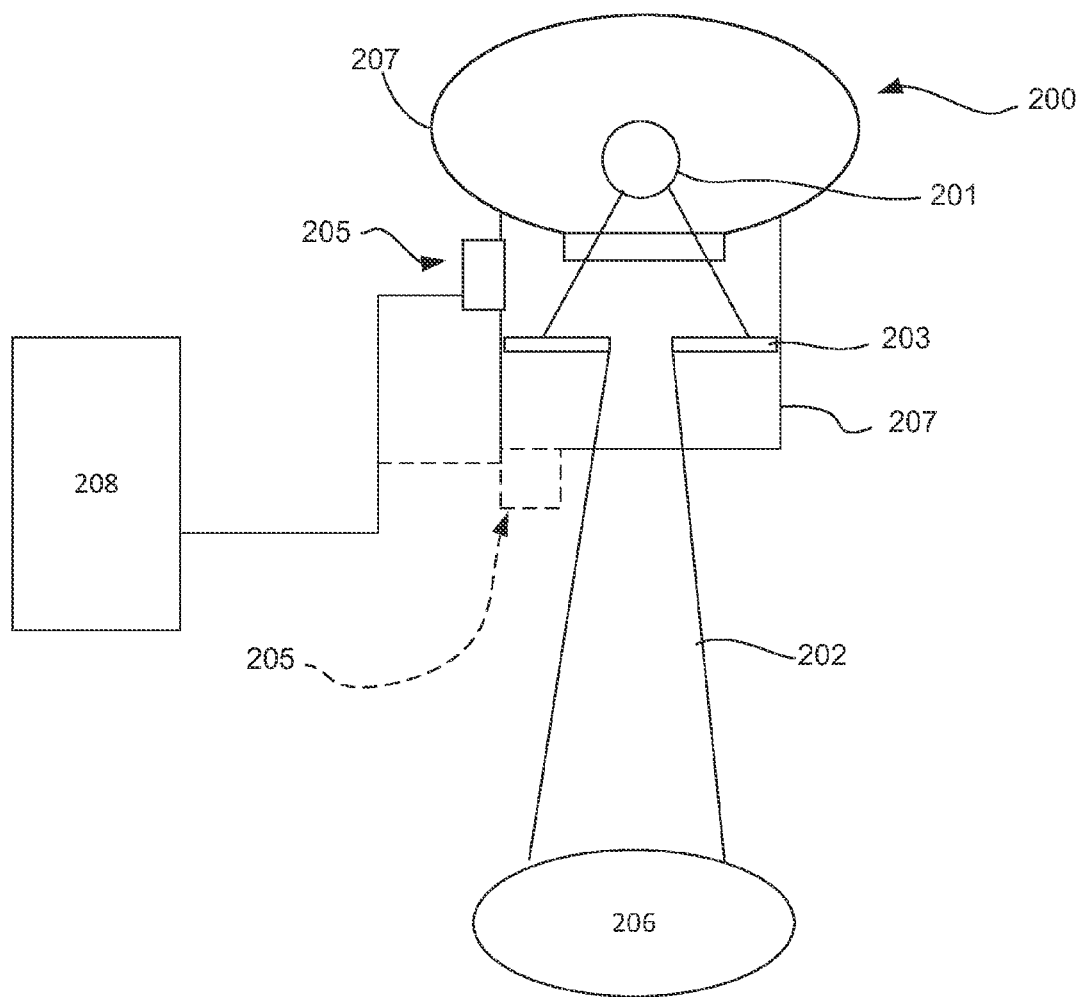
FIG. 2a illustrates schematically an exemplary X-ray source according to present invention.

FIG. 2a is a schematic view of a simplified X-ray source housing 200. The X-ray source housing 200 comprises an X-ray tube 201, which generates X-rays 202 with a certain formation (ray image). The X-rays 202 pass through a collimator 203, which narrows the beam before radiating an object 206 to be examined.

According to the invention, at least one x-ray measuring detector 205 is arranged adjacent to the x-ray source housing 200, between the tube 201 and the object (e.g. patient) 206 to be examined.

The source housing comprises a housing 207. The detector 205 may be mounted adjacent to the tube on the housing, in a first position as illustrated by solid line or in position where the beam exits the housing, as illustrated by dashed line. In this way, when the tube generates a ray formation with a primary ray portion for radiating the object, the detector positioned outside the primary ray portion but inside the ray formation (ray image).

Figure 2B:
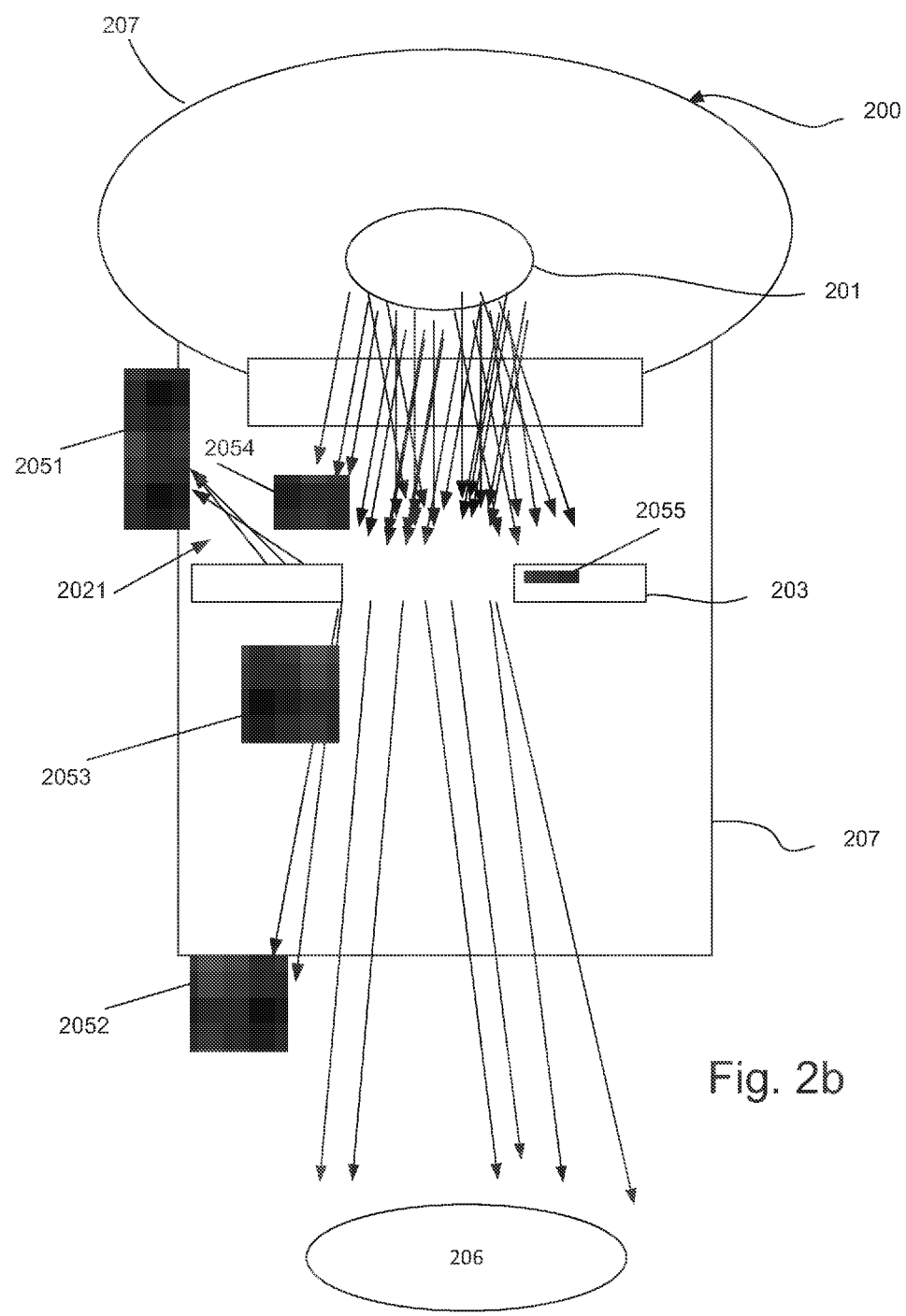

FIG. 2b illustrates a number of different positions in which the detector(s) (black boxes) may be provided.

Detector 2051 is arranged on the housing 207 and is configured to detect the scattered rays 2021. In this case an aperture is provided in the housing to let through the rays.

Detector 2052 is arranged at the opening of the housing 207 from which x-rays emerge. The detector may, at least partly or entirely, be arranged in the image field, i.e. the ray formation that will radiate the object to be examined. However, due to its position on the fringe of the opening, its influence on the reproduced image will be negligible or very little.

Detector 2053 is arranged inside the housing 207, beneath the collimator 203 aperture. Although, in this embodiment, the detector may, at least partly or entirely, be arranged in the image field, i.e. the ray formation that will radiate the object to be examined. However, due to its position on the fringe of the beam formation, its influence on the reproduced image will be negligible or very little.

Detector 2054 is arranged inside the housing 207, between the tube and the collimator 207. In this case, the primary beam before passing the collimator will be measured and the reproduced image will not be influenced at all.

Detector 2055 is arranged inside or on a surface of the collimator 203. In this case, the primary beam before passing the collimator will be measured and the reproduced image will not be influenced at all.

The consequence of positioning of the detector(s) 205 in a space adjacent to the source 201 or in small portion of sight for the primary X-ray beams 202, is that the detector will not interfere or have very small (negligible) with the rays radiating the object 206 and deteriorate the reproduced image.

The X-ray measuring detector 205 (which will be detailed below) comprises a sensor, which is configured to measure radiological parameters, mainly dose of scattered X-rays. The sensor is also capable of measuring other radiological parameters such as dose rate, Peak Kilovoltage (kVp), half-value layer (HVL), total filtration, exposure time, pulses, pulse rate and dose/pulse.

The output of the detector may be provided to a computer unit 208 for processing the signals.

The detector 205 may be assembled on the source housing separately or built in.

Figure 3:
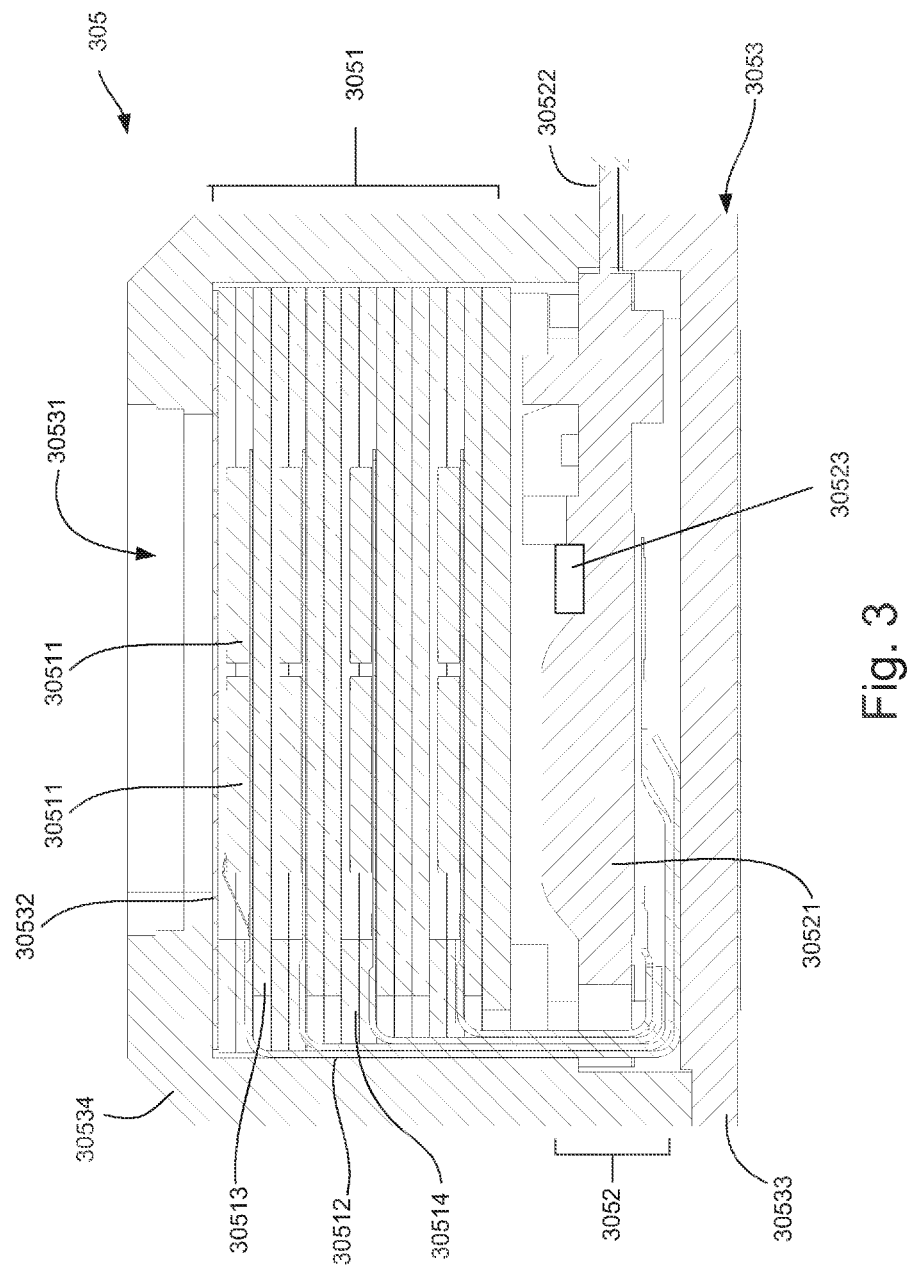
FIG. 3 is a cut through an exemplary detector according to one embodiment of the present invention.

FIG. 3 is a cross sectional view of one exemplary detector 305 according to one embodiment of the invention. The detector comprises a sensor part 3051 and electronics 3052 enclosed inside a housing 3053.

The housing 3053, e.g. made of tin or other suitable x-ray blocking material, has an open end (window) 30531 for allowing through radiation. The open end is however, provided with a light blocking element 30532. The housing comprises a bottom portion 30533 and a upper portion 30534.

The sensor part 3051 comprises a number of stacked solid state (silicon) diodes 30511 (four rows in this case). Diodes in each row are arranged on a carrier (PCB) (not numbered) connected to a conductor 30512.

A filtering layer 30513, e.g. made of copper or other suitable material, is arranged between each row comprising diodes and carrier. The rows are distanced using distancing elements 30514 (at each side), e.g. arranged as a frame for each row. The filter layers function as filters between each diode row such that they block radiation from sides but allow radiation falling through the open end 30531 of the housing.

The electronic portion comprises 3052 a signal processing unit 30521 (e.g. realized as Application Specific Integrated Circuit (ASIC)). Each row is connected to input of processing unit by means of conductors 30512 as a channel. The output of the signal processing unit may be connected to external processing elements (not shown) through a cable 30522. Instead or in combination with the cable 30522, the electronic portion may also be provided with a RF transmitter/receiver 30523 for transmitting processed data to a receiver. The electronics may be provided with power using onboard power source or external power source.

The number of diodes in rows and number of layers depends on application are. The detector may comprise only one diode, e.g. for the applications where the sensor is incorporated with the collimator as described above. However, a preferred embodiment comprises at least three or more layers.

As mentioned earlier, the sensor comprises stacked diodes, in which each diode layer is radiated by same source radiation. The filter layers between each diode layer changes energy content of the source radiation, i.e. each diode layer is radiated by spectrally different radiation although having a common source radiation. Each diode layer generates a current depending on the radiation intensity and energy. The diode currents are connected to an amplifier (e.g. transimpedance amplifier) with varying amplification and a following amplifier (e.g. voltage amplifier) with varying amplification. The diode specific voltage for each diode layer is then forwarded to an Analogue-to-Digital converter (ADC) for further connection to a processing unit, which processes the signals to compute one or several of dose, kVp, total filter, dose rate, expose time, HVL, etc., for the source radiation.

Figure 4:
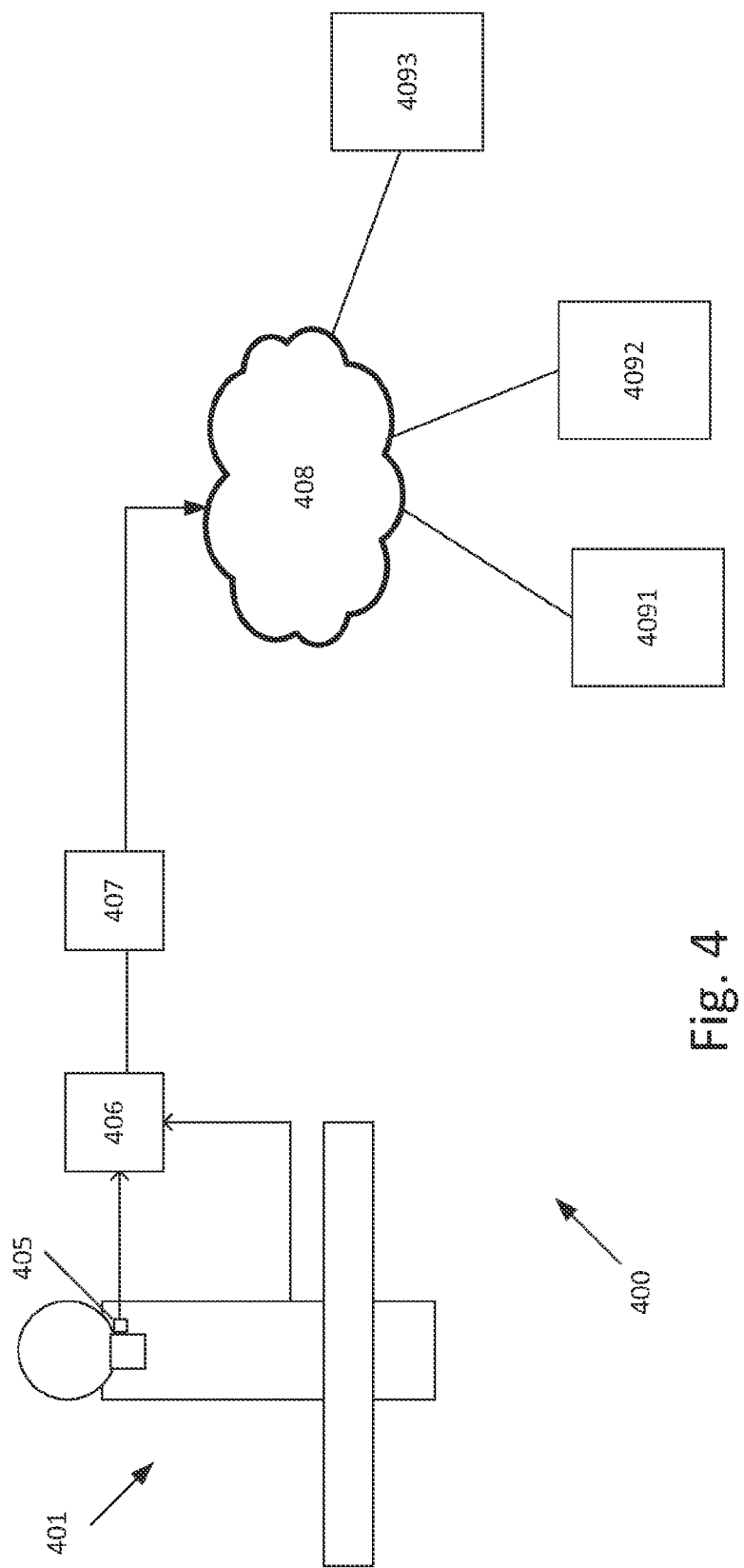
FIG. 4 is a schematic communication system for radiography purposes incorporating present invention.

FIG. 4 illustrates a schematic of a network 400, which may incorporate a detector and measuring teachings of the present invention. The network according to this embodiment comprises an X-ray examination arrangement 401, such an X-ray machine, CT, radiography machine, etc., provided with at least one detector 405 as described earlier. The examination arrangement 401 and the detector 405 may be connected to RIS/PACS 406 and/or a data collector 407. The information from data collector 407 may be provided to a database 408 in the computer network.

The database may consist of a cloud-based application and a locally-installed DICOM or similar (MWL, RDSR, MPPS, DICOMOCR) data collector.

Users such as, operator 4091, RSO physicist 4092, radiologist 4093 etc., may access the information form the examination arrangement or detector, for example through a web browser. This enables all individuals in the workflow easy access to the solution without any troublesome software installations.

The data collector may be a software solution that may be installed at examination site. The data collector connects the X-ray machines and/or RIS/PACS systems using the DICOM network.

The foregoing description of embodiments of the present invention, have been presented for purposes of illustration and description. The foregoing description is not intended to be exhaustive or to limit embodiments of the present invention to the precise form disclosed, and modifications and variations are possible in light of the above teachings or may be acquired from practice of various embodiments of the present invention. The embodiments discussed herein were chosen and described in order to explain the principles and the nature of various embodiments of the present invention and its practical application to enable one skilled in the art to utilize the present invention in various embodiments and with various modifications as are suited to the particular use contemplated. The features of the embodiments described herein may be combined in all possible combinations of methods, apparatus, modules, systems, and computer program products.

It should be noted that the word "comprising" does not exclude the presence of other elements or steps than those listed and the words "a" or "an" preceding an element do not exclude the presence of a plurality of such elements. It should further be noted that any reference signs do not limit the scope of the claims, that the invention may be implemented at least in part by means of both hardware and software, and that several "means", "units" or "devices" may be represented by the same item of hardware.

Software and web implementations of various embodiments of the present invention can be accomplished with standard programming techniques with rule-based logic and other logic to accomplish various database searching steps or processes, correlation steps or processes, comparison steps or processes and decision steps or processes. It should be noted that the words "component" and "module," as used herein and in the following claims, is intended to encompass implementations using one or more lines of software code, and/or hardware implementations, and/or equipment for receiving manual inputs.

The various embodiments of the present invention described herein is described in the general context of method steps or processes, which may be implemented in one embodiment by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), etc. Generally, program modules may include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps or processes.

What we claim is:

1. An X-ray parameter measuring arrangement comprising a detector for measuring an x-ray parameter, the arrangement being configured to be positioned in a position adjacent to an x-ray source arranged to generate a ray formation for radiating an object, wherein said position is in a primary ray portion such that the interference with a reproduced image is reduced or eliminated, the detector comprising:
   a housing;
   a number of stacked layers enclosed in the housing, the number of stacked layers including at least a first layer comprising a first diode layer and a second layer comprising a second diode layer, wherein the first diode layer and the second diode layer detect the generated ray formation;
   a radiation filter positioned between said first diode layer and said second diode layer; and
   a processing unit included as one of said number of stacked layers, wherein the processing unit is:
      positioned under said first diode layer and said second diode layer;
      connected to said first diode layer and said second diode layer; and
      configured to output a signal corresponding to a parameter of the ray formation based on the detection of the ray formation by the first diode layer and the second diode layer.

2. The X-ray parameter measuring arrangement of claim 1, wherein the detector is configured to measure scattered radiation.

3. The X-ray parameter measuring arrangement of claim 1, wherein the detector is configured to measure a direct radiation.

4. The X-ray parameter measuring arrangement of claim 1, wherein the detector is arranged on a housing of the x-ray source and configured to detect the scattered rays through an aperture provided in the housing.

5. The X-ray parameter measuring arrangement of claim 1, wherein the detector is arranged at an opening of a housing of the source from which x-rays emerge, positioned at least partly or entirely in an image field, i.e. the ray formation radiating an object to be examined.

6. The X-ray parameter measuring arrangement of claim 1, wherein the detector is arranged inside a housing of the source, in a position of corresponding to a direction from where the rays leave a collimator aperture positioned at least partly or entirely in an image field, i.e. the ray formation radiating an object to be examined.

7. The X-ray parameter measuring arrangement of claim 1, wherein the detector is arranged inside a housing, between the source and a collimator.

8. The X-ray parameter measuring arrangement of claim 1, wherein the detector is arranged inside or on a surface of a collimator.

9. The X-ray parameter measuring arrangement of claim 1, configured to measure one or several radiological parameters including dose of scattered X-rays, total dose, dose rate, Peak Kilovoltage (kVp), half-value layer (HVL), total filtration, exposure time, pulses, pulse rate and dose/pulse.

10. The X-ray parameter measuring arrangement of claim 1, wherein the detector comprises a RF communication portion.

11. An X-ray detector comprising:
   a housing,
   a number of stacked layers enclosed in said housing, the number of stacked layers including at least a first layer comprising a first diode layer and a second layer comprising a second diode layer, wherein the first diode layer and the second diode layer detect x-rays;
   a radiation filter positioned between said first diode layer and said second diode layer; and
   a processing unit included as one of said number of stacked layers, wherein the processing unit is:
      positioned under said first diode layer and said second diode layer;
      connected to said first diode layer and said second diode layer; and configured to output a signal corresponding to a parameter of the x-rays based on the detection of the x-rays by the first diode layer and the second diode layer.

12. The X-ray detector of claim 11, further comprising a housing of a radiation blocking material.

13. The X-ray detector of claim 11, wherein said processing unit is realized in Application Specific Integrated Circuit (ASIC).

14. A computer network for handling radiological information, the network comprising an X-ray examination arrangement, a data collector and a database, wherein the X-ray examination arrangement is provided with an X-ray parameter measuring arrangement comprising a detector for measuring said x-ray parameter, the arrangement is configured to be positioned in a position adjacent to an x-ray source arranged to generate a ray formation having a primary ray portion for radiating an object, wherein said detector is arranged in said primary ray portion such that the interference with a reproduced image is reduced or eliminated and the detector comprises:
   a housing;
   a number of stacked layers enclosed in the housing, the number of stacked layers including at least a first layer comprising a first diode layer and a second layer comprising a second diode layer, wherein the first diode layer and the second diode layer detect the generated ray formation;
   a radiation filter positioned between said first diode layer and said second diode layer; and
   a processing unit included as one of said number of stacked layers, wherein the processing unit is:
      positioned under said first diode layer and said second diode layer;
      connected to said first diode layer and said second diode layer; and
      configured to output a signal corresponding to a parameter of the ray formation based on the detection of the ray formation by the first diode layer and the second diode layer.

15. The computer network of claim 14, wherein the database consist of a central application and a locally-installed DICOM or MWL, RDSR, MPPS, DICOMOCR data collector.

* * * * *